US009869651B2

(12) United States Patent
Akinwande et al.

(10) Patent No.: US 9,869,651 B2
(45) Date of Patent: Jan. 16, 2018

(54) ENHANCED SENSITIVITY OF GRAPHENE GAS SENSORS USING MOLECULAR DOPING

(71) Applicant: Board of Regents, The University of Texas System, Austin, TX (US)

(72) Inventors: Deji Akinwande, Austin, TX (US); Seyedeh Maryam Mortazavi Zanjani, Austin, TX (US); Mir Mohammad Sadeghi, Austin, TX (US); Milo Holt, Pflugerville, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 15/497,413

(22) Filed: Apr. 26, 2017

(65) Prior Publication Data

US 2017/0315075 A1    Nov. 2, 2017

Related U.S. Application Data

(60) Provisional application No. 62/329,780, filed on Apr. 29, 2016.

(51) Int. Cl.
*H01L 27/092* (2006.01)
*H01L 29/16* (2006.01)
(Continued)

(52) U.S. Cl.
CPC ....... *G01N 27/125* (2013.01); *G01N 33/0036* (2013.01); *G01N 33/0054* (2013.01);
(Continued)

(58) Field of Classification Search
CPC .......... G01N 33/0054; G01N 33/0036; G01N 27/125; H01L 27/0092; H01L 29/1606; H01L 29/78684; H01L 23/522
See application file for complete search history.

(56) References Cited

U.S. PATENT DOCUMENTS

2013/0018599 A1* 1/2013 Peng ................. B82Y 15/00
    702/30
2015/0059471 A1* 3/2015 Haque ................ G01N 19/10
    73/335.05

OTHER PUBLICATIONS

Mortazavi Zanjani, Seyedeh Maryam, et al. "Enhanced sensitivity of graphene ammonia gas sensors using molecular doping." Applied Physics Letters 108.3 (2016); 5 pages, Jan. 19, 2016.
(Continued)

*Primary Examiner* — Jennifer Wecker
(74) *Attorney, Agent, or Firm* — Baker Botts L.L.P.

(57) ABSTRACT

The sensitivity of a graphene gas sensor to a gas analyte molecule may be significantly enhanced using molecular doping, which may be as effective as substitutional doping and more effective than electric-field doping. In particular, the room temperature sensitivity of $NO_2$-doped graphene to $NH_3$ was measured to be comparable to the sensitivity of graphene doped with substitutional boron atoms and superior to that of undoped graphene by an order of magnitude. The detection limit for $NO_2$-doped graphene gas sensors was estimated to be about 200 ppb, which may be improved with extended exposure to $NO_2$, compared to a detection limit of about 1.4 ppm for undoped graphene. While the stability analysis of $NO_2$-doped graphene sensors indicates that the doping method may not be completely stable, molecular doping is nevertheless a candidate technique for sensitivity improvement by enhancing the initial carrier concentration.

16 Claims, 6 Drawing Sheets

(51) Int. Cl.
  *H01L 23/52* (2006.01)
  *G01N 33/00* (2006.01)
  *G01N 27/12* (2006.01)
  *H01L 23/522* (2006.01)
  *H01L 29/786* (2006.01)

(52) U.S. Cl.
  CPC ........ *H01L 27/092* (2013.01); *H01L 29/1606* (2013.01); *H01L 23/522* (2013.01); *H01L 29/78684* (2013.01)

(56) References Cited

OTHER PUBLICATIONS

Mortazavi Zanjani, Seyedeh Maryam, "Heterogeneous Integration of Graphene and Si CMOS for Gas Sensing." Dissertation, 2014; 130 pages, 2014.

\* cited by examiner

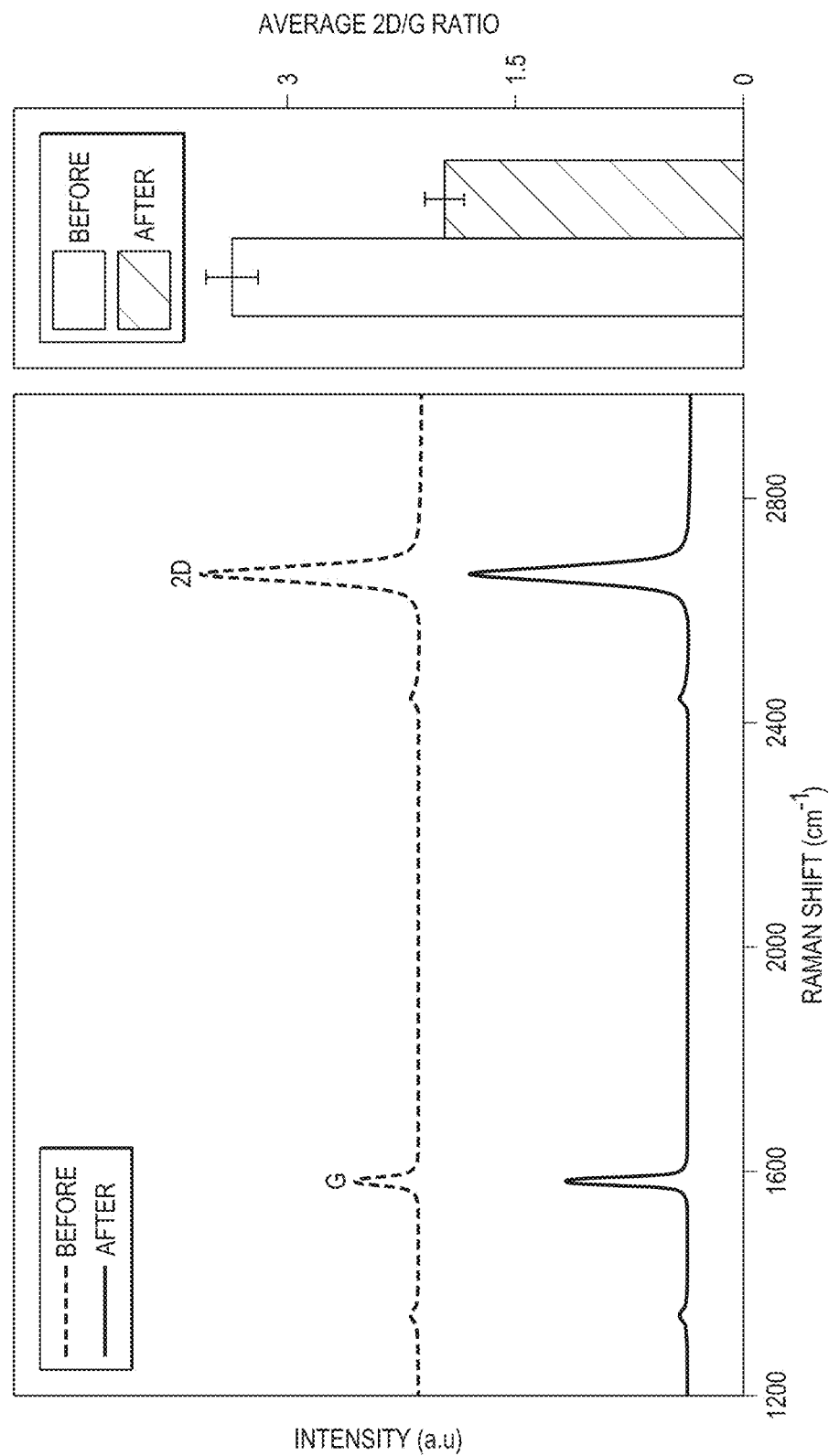

ENHANCED SENSITIVITY OF GRAPHENE GAS SENSORS USING MOLECULAR DOPING

CROSS REFERENCE TO RELATED APPLICATIONS

This application claims priority from U.S. Provisional Patent Application No. 62/329,780, filed Apr. 29, 2016, entitled "ENHANCED SENSITIVITY OF GRAPHENE GAS SENSORS USING MOLECULAR DOPING".

BACKGROUND

Field of the Disclosure

This disclosure relates generally to gas sensors and, more particularly, to enhanced sensitivity of graphene gas sensors using molecular doping.

Description of the Related Art

Detecting presence of gas molecules is of prominent importance for controlling chemical processes, safety systems, and industrial and medical applications. Despite enormous progress in developing and improving various types of gas sensors, sensors with higher sensitivity, lower sensing limit, and lower cost that can perform at room temperature remain desirable. Graphene is a promising candidate for gas sensing applications due to its unique transport properties, exceptionally high surface-to-volume ratio, and low electrical noise.

BRIEF DESCRIPTION OF THE DRAWINGS

For a more complete understanding of the present disclosure and its features and advantages, reference is now made to the following description, taken in conjunction with the accompanying drawings, in which:

FIG. 5 illustrates selected elements of Raman spectra of graphene gas sensors.

SUMMARY

Figure 1A:
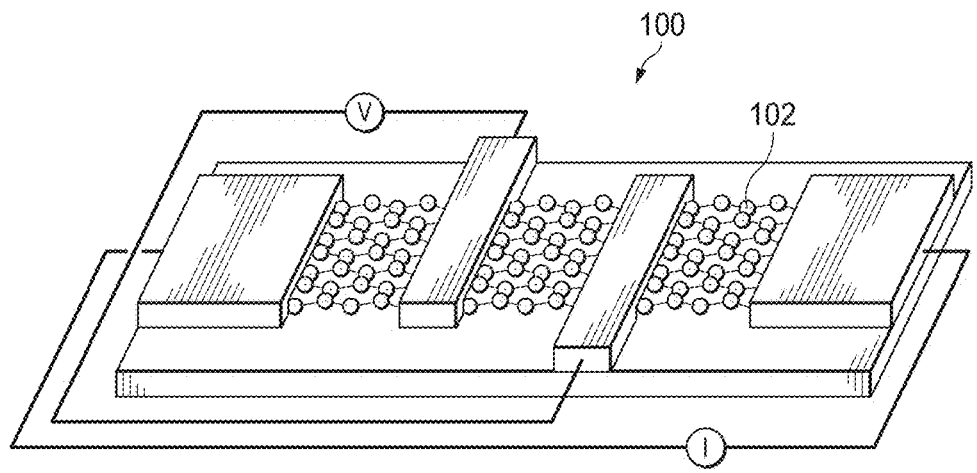
FIGS. 1A and 1B illustrate selected elements of an example of a graphene gas sensor for enhanced sensitivity using molecular doping.

In one aspect, a graphene gas sensor is disclosed. The graphene gas sensor may include a graphene element molecularly doped with nitrogen dioxide ($NO_2$), a pair of voltage electrodes spaced apart on the graphene element, and a pair of current electrodes at each end of the graphene element. In the graphene gas sensor, the graphene element may be used to detect ammonia ($NH_3$) based on a conductivity of the graphene element measured using the pair of voltage electrodes and the pair of current electrodes. In the graphene gas sensor, a change in the conductivity upon exposure to $NH_3$ may be greater for the graphene element doped with $NO_2$ than an undoped graphene element.

In any of the disclosed embodiments of graphene gas sensor, the graphene gas sensor may be included in a complementary metal oxide semiconductor (CMOS) device.

In any of the disclosed embodiments of graphene gas sensor, the graphene element may be molecularly doped with $NO_2$ using 100 ppm of $NO_2$ in $N_2$ at 500 Torr pressure and at room temperature. In any of the disclosed embodiments of graphene gas sensor, the graphene element may be molecularly doped for a duration between 10 minutes and 60 minutes.

In any of the disclosed embodiments of graphene gas sensor, the conductivity may be measured by applying a current using the pair of current electrodes, measuring a voltage using the pair of voltage electrodes, and determining the conductivity based on the current and the voltage. In any of the disclosed embodiments of graphene gas sensor, the voltage may be measured using a field effect transistor.

In any of the disclosed embodiments of graphene gas sensor, the graphene element may include a single atomic layer of carbon.

In any of the disclosed embodiments, the graphene gas sensor may further include a silicon substrate on which the graphene element is situated.

In a further aspect, a method of detecting ammonia ($NH_3$) gas is disclosed. The method may include applying a current to a graphene element molecularly doped with nitrogen dioxide ($NO_2$), measuring a voltage across the graphene element, and exposing the graphene element to $NH_3$ gas while measuring a change in the voltage. In the method, the change in the voltage may be indicative of the concentration of the $NH_3$ gas. In the method, the change in voltage may be greater for the graphene element doped with $NO_2$ than an undoped graphene element.

In any of the disclosed embodiments of the method, the graphene element may be implemented in a complementary metal oxide semiconductor (CMOS) device.

In any of the disclosed embodiments, the method may further include molecularly doping the graphene element with $NO_2$ using 100 ppm of $NO_2$ in $N_2$ at 500 Torr pressure and at room temperature. In the method, molecularly doping the graphene element may further include molecularly doping the graphene element for a duration between 10 minutes and 60 minutes.

In any of the disclosed embodiments, the method may further include determining a conductivity of the graphene element. In the method, determining the conductivity of the graphene element may further include applying the current using a pair of current electrodes spaced apart on the graphene element, measuring a voltage using a pair of voltage electrodes spaced apart on the graphene element, and determining the conductivity based on the current and the voltage.

In any of the disclosed embodiments of the method, measuring the voltage may further include measuring the voltage using a field effect transistor.

In any of the disclosed embodiments of the method, the graphene element may include a single atomic layer of carbon.

In any of the disclosed embodiments of the method, the graphene element may be situated on a silicon substrate.

DETAILED DESCRIPTION

In the following description, details are set forth by way of example to facilitate discussion of the disclosed subject matter. It should be apparent to a person of ordinary skill in the field, however, that the disclosed embodiments are exemplary and not exhaustive of all possible embodiments.

As noted previously, gas sensors of increasingly greater sensitivity, faster response time and portability are desired for many industrial applications. Furthermore, a gas sensor that is coupled with back-end complimentary metal-oxide semiconductor (CMOS) amplification and analysis circuitry also provides advantages from tighter system integration, which may improve functionality and may lower power consumption and cost.

Current electrochemical sensors may provide suitable response times for certain applications, but may have inherently limited response time due to diffusion processes through an electrolyte. Furthermore, solid state metal oxide semiconductor (MOS) sensors may suffer from high internal resistance, and may be operational at high temperatures to activate the MOS surface. Oxygen from the air may bind to the surface at high temperatures (usually >400 C) to form an active sensing layer at the MOS surface, while the sensing mechanism of MOS sensors may be a redox reaction between the gas analyte and the MOS surface. As a result, MOS sensors may be difficult to integrate in a low-power CMOS package.

The discovery of graphene and the subsequent progress in nanotechnology and nanomaterials have led to ultra-sensitive room-temperature sensors that can detect individual analyte molecules, such as nitrogen dioxide ($NO_2$). Certain key factors of graphene as a sensor material include unique transport properties, extremely high surface-to-volume ratio, and low electrical noise. Electronic states of graphene may be affected by adsorbed gas molecules and the charge transfer between graphene and the adsorbed gas molecules can modify carrier concentration without altering mobility.

However, pristine suspended graphene may not perform particularly well as a gas sensor. The reported sensitivity for graphene gas sensors can be attributed to physical or chemical functionalization of graphene by adsorbates, defects, and the supporting substrate. While such molecular modifications may be determinative for the observed sensitivity of graphene sensors to certain gas molecule analytes, more controllable molecular functionalization methods for graphene may be applied to achieve higher sensitivity. The detection of individual $NO_2$ molecules using graphene has been observed through a statistical analysis of a prolonged measurement result under strictly defined conditions, rather than a more practical method, such as with a resistive graphene gas sensors, in which the analyte is immediately detected through a change in resistance of the graphene upon exposure to the analyte molecule. Theoretical calculations and recent published scientific results have indicated improvement to the sensitivity of graphene sensors can be achieved by introducing substitutional impurities, which cause localized perturbations in structure and electronic states of graphene and lead to higher binding energy and charge transfer between graphene and the analyte gas molecules.

Despite extensive information revealed by theoretical studies on the interaction of suspended pristine graphene and gas molecules, the sensing mechanisms for actual fabricated graphene transducers are expected to be more complex than the theoretical models due to the effects of unintentional adsorbates and the supporting substrate. Indeed, the adsorption capacity of graphene for gas molecules predicted by theoretical calculations is smaller than experimental values by almost two orders of magnitude. Compared to substitutional impurities, molecular doping via adsorbed molecules weakly modifies the electronic properties of graphene with minimal effects on molecular structure because of the strong carbon-carbon $sp^2$ bonds of graphene.

As will be described in further detail, molecular doping may be used to functionalize graphene to increase graphene's binding energy and, thereby, sensitivity to specific gas molecules. Enhanced sensitivity of graphene gas sensors using molecular doping may provide high sensitivity, low response time, low-power room temperature operation, and ease of electronic integration, such as with wireless interfaces. Specifically, it was determined that molecular doping of graphene using $NO_2$ enhances sensitivity of graphene to ammonia ($NH_3$) gas molecules. It was discovered that the adsorption of $NO_2$ molecules to graphene may increase sensitivity of graphene to $NH_3$ molecules by more than an order of magnitude.

Figure 1B:
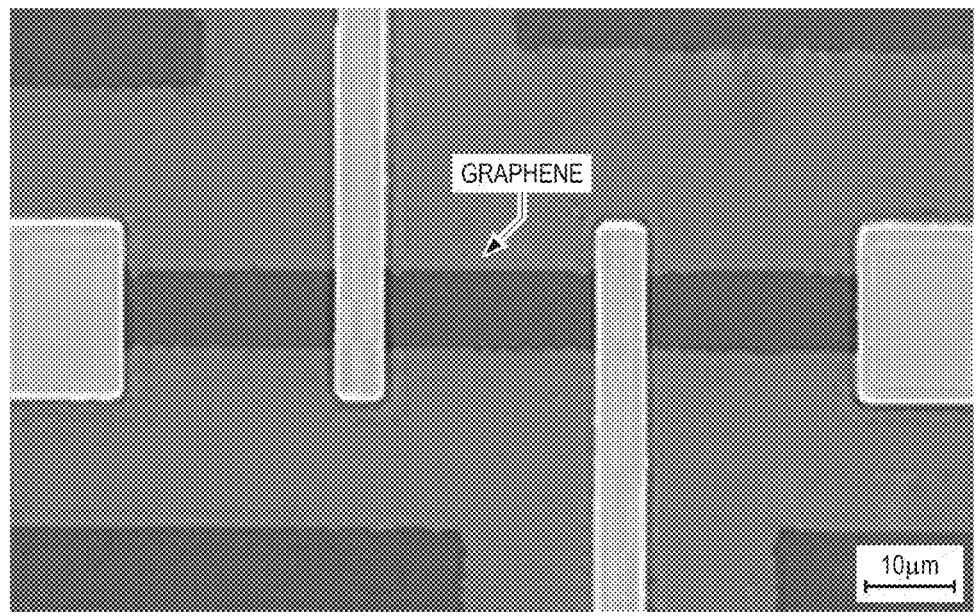

Turning now to the drawings, FIGS. 1A-1B illustrate selected elements of an example of a graphene gas sensor 100 for enhanced sensitivity using molecular doping. A 3-dimensional rendered view is shown as FIG. 1A as a perspective schematic illustration, while a scanning electron microscopy (SEM) image from a top view is shown as FIG. 1B. As shown in FIG. 1A, graphene gas sensor 100 is a resistive sensor with four-probe electrical connections and back-gated graphene field-effect transistors (GFETs). A graphene channel 102 was formed with a length of about 10 μm and a width of about 25 μm between electrodes. It is noted that FIG. 1A is not drawn to scale and is a schematic illustration.

The graphene used in graphene gas sensor 100 of FIGS. 1A and 1B was synthesized via chemical vapor deposition (CVD). The CVD graphene was transferred to a silicon substrate covered with 300 nm thick $SiO_2$, which was thermally grown via a poly(methyl methacrylate) PMMA-supported wet-transfer process. The thickness and quality of graphene samples was evaluated with Raman spectroscopy (see FIG. 5), using a neodymium-doped yttrium aluminum garnet (Nd:YAG) laser at 532 nm wavelength under ambient conditions. The undoped graphene samples showed a symmetric 2D peak with full width at half maximum (FWHM) of about 28 $cm^{-1}$, a 2D peak to G peak intensity ratio (I(2D)/I(G)) greater than about 3, and a negligible ratio of D peak to G peak intensity (I(D)/I(G)), which is indicative of high quality monolayer graphene (e.g. a single atomic layer of carbon atoms). Graphene channel 102 on a $Si/SiO_2$ substrate was patterned using electron beam lithography and etched using a low-power reactive-ion-etch process in oxygen plasma. Electrical connections to graphene channel 102 were made using electron beam lithography followed by deposition of chromium Cr (5 nm)/gold Au (45 nm) using e-beam evaporation and a lift-off process. During measurements, the gas concentration in the measurement chamber was controlled using mass flow controllers (MFCs) ahead of a mixing manifold, with $N_2$ as a diluting gas. At the gas sources, concentration of $NH_3$ and $NO_2$ gases was 100 parts per million (ppm) in dry air. The experiments described herein were carried out at a constant flow of gas at 500 Torr pressure and at room temperature.

As shown in FIG. 1A, conductivity measurements of graphene channel 102 were performed using the four-probe electrical connections. For example, a current (I) may be applied and a corresponding voltage (V) may be measured to determine conductivity.

Figure 2A:
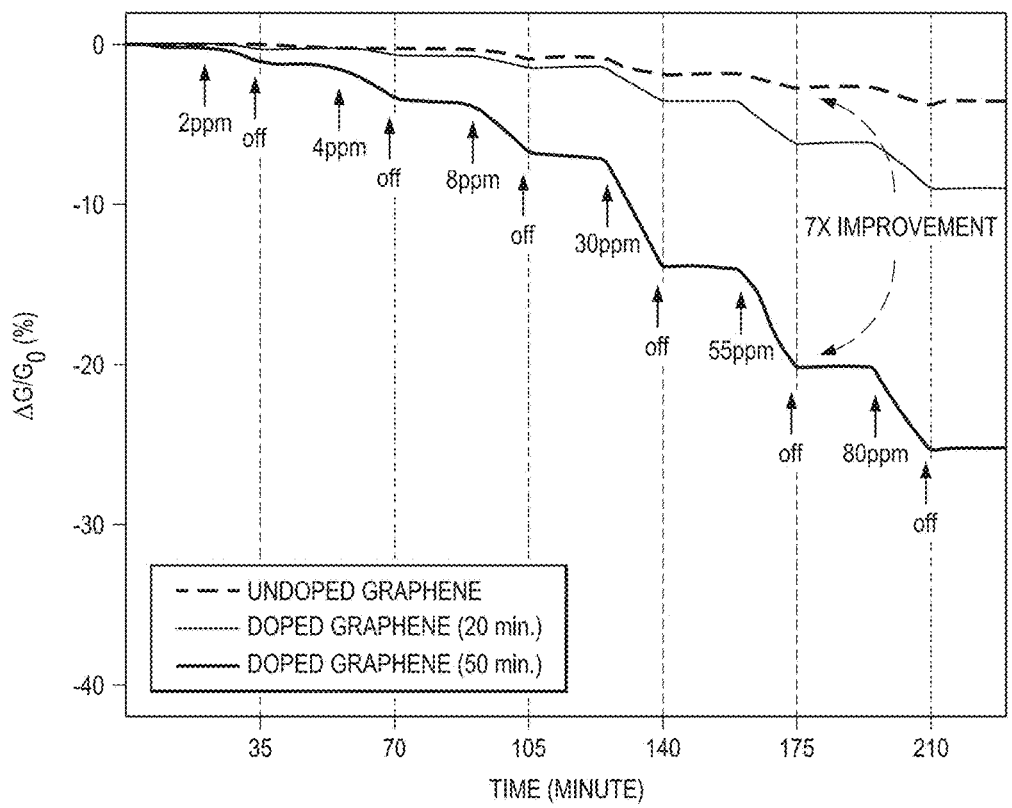
FIGS. 2A and 2B illustrate selected elements of data plots showing sensitivity of graphene gas sensors.
Figure 2B:
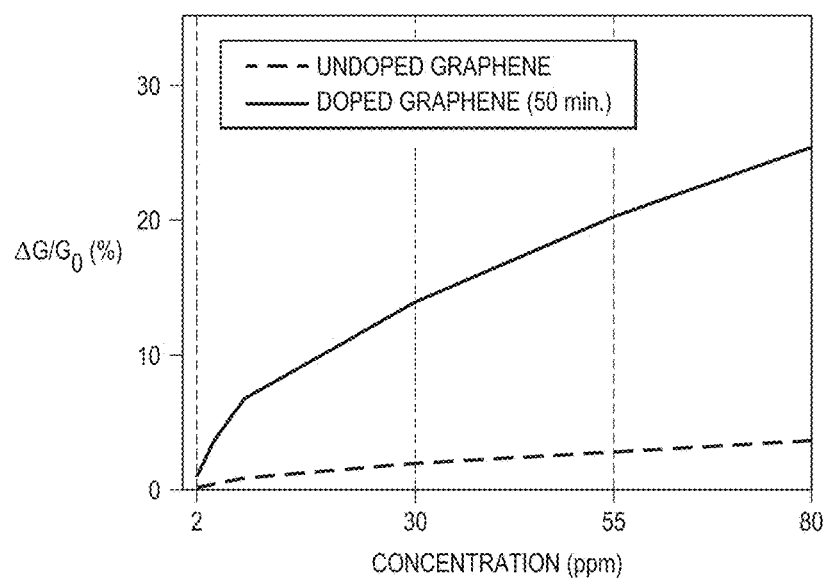

Referring now to FIGS. 2A and 2B, selected elements of data plots showing sensitivity of graphene gas sensors are illustrated. In FIG. 2A sensitivity of undoped graphene and $NO_2$-doped graphene sensors to $NH_3$ gas is shown, while in FIG. 2B sensitivity as a function of $NH_3$ concentration for undoped and $NO_2$-doped graphene is illustrated. FIG. 2A shows sensitivity of a graphene gas sensor, such as graphene gas sensor 100 depicted in FIG. 1A, before and after doping with $NO_2$ under exposure to various concentrations of $NH_3$, from 2 ppm to 80 ppm $NH_3$. The sensitivity is defined as the change of electrical conductance ($\Delta G$) normalized to an initial value of the electrical conductance ($G_0$). The graphene gas sensor was exposed to different concentrations of $NH_3$ for 15 min., followed by 20 min. of $N_2$ purge. As shown in FIG. 2b, sensitivity of the graphene gas sensor before doping with $NO_2$ is 3.7% for 80 ppm $NH_3$, which is comparable to other prior reports. For concentrations below 8 ppm $NH_3$, the sensitivity of the graphene gas sensor before doping with $NO_2$ is less than 1%. The $NH_3$ sensitivity measurements were repeated after the graphene gas sensor was doped by $NO_2$. For doping, graphene was exposed to 100 ppm of $NO_2$ gas for 50 min. at 500 Torr and room temperature, which shifted the Dirac point voltage ($V_{Dirac}$) from 18V to 165 V. The response of $NO_2$-doped graphene gas sensor to various concentrations of $NH_3$ is depicted in FIG. 2B (Doped Graphene (50 min)). TABLE 1 contains the sensitivity of graphene gas sensors before and after $NO_2$-doping, which is shown in FIG. 2B.

TABLE 1

Conductance sensitivity of graphene gas sensors using undoped and doped graphene in FIG. 2B.

| Graphene Type | 2 ppm $NH_3$ | 4 ppm $NH_3$ | 8 Ppm $NH_3$ | 30 ppm $NH_3$ | 55 ppm $NH_3$ | 80 ppm $NH_3$ |
|---|---|---|---|---|---|---|
| Undoped | 0.1% | 0.4% | 0.9% | 1.9% | 2.7% | 3.7% |
| $NO_2$-doped | 1.1% | 3.4% | 6.8% | 13.9% | 20.2% | 25.3% |

The results in FIGS. 2A and 2B and TABLE 1 show that doping graphene with $NO_2$ significantly increases the sensitivity of graphene to $NH_3$. Compared to the undoped graphene gas sensor, the sensitivity of $NO_2$-doped graphene to 2 ppm $NH_3$ is increased by 11-fold, and to 80 ppm of $NH_3$ is increased by 7-fold. The sensitivity of the $NO_2$-doped graphene to $NH_3$ is comparable to the reported sensitivity for boron-doped graphene, which is a structural substitutional doping, under continuous UV light illumination. FIGS. 2A and 2B and TABLE 1 show that for improving sensitivity of graphene resistance to adsorption of gas molecules, molecular doping can be as effective as substitutional doping. Moreover, improving the sensitivity by an order of magnitude at low analyte concentrations may indicate an improved detection limit of $NO_2$-doped graphene to $NH_3$, which was not directly verified. The detection limit of $NO_2$-doped graphene gas sensors, such as depicted in FIG. 1A, is estimated to be about 200 ppb $NH_3$, compared to about 1.4 ppm $NH_3$ using undoped graphene. To estimate the detection limit, it was assumed that sensitivity is proportional to gas concentration, such that the sensitivity versus concentration curve at low concentrations may be extrapolated to calculate the $NH_3$ concentration that causes a ratio of $\Delta G/G_0$ Raman peaks comparable to the measurement noise for $\Delta G/G_0$ peaks. In addition, it was observed that the sensitivity of $NO_2$-doped graphene to $NH_3$ molecules was proportional to the duration of $NO_2$ doping.

The Doped Graphene (20 min.) curve in FIG. 2A shows the sensitivity of the graphene gas sensor when exposed to 100 ppm of $NO_2$ gas for only 20 min. FIG. 2A also shows, that after $NH_3$ exposure, the conductance remains nearly stable suggesting that resetting the sensor may involve additional actions such as UV light irradiation, and thermal annealing, which can be performed through Joule heating of the graphene. However, the stability of the adsorbed dopant molecules, $NO_2$ molecules in this case, during the resetting process might be a concern. To address this concern, graphene may be doped using another molecule that chemisorbs to the graphene and can withstand the resetting process of the sensor. Alternatively, a modified fabrication procedure may be employed. For example, graphene may be doped with $NO_2$ or another molecule and then transferred to the substrate such that the doped side, which is the exposed side of graphene during the doping process, comes in contact with the substrate. In this arrangement, the $NO_2$ molecules are trapped between the substrate and the graphene, and the impermeability of graphene to molecules may prevent the $NO_2$ molecules from escaping during the resetting process of the sensor.

Figure 3A:
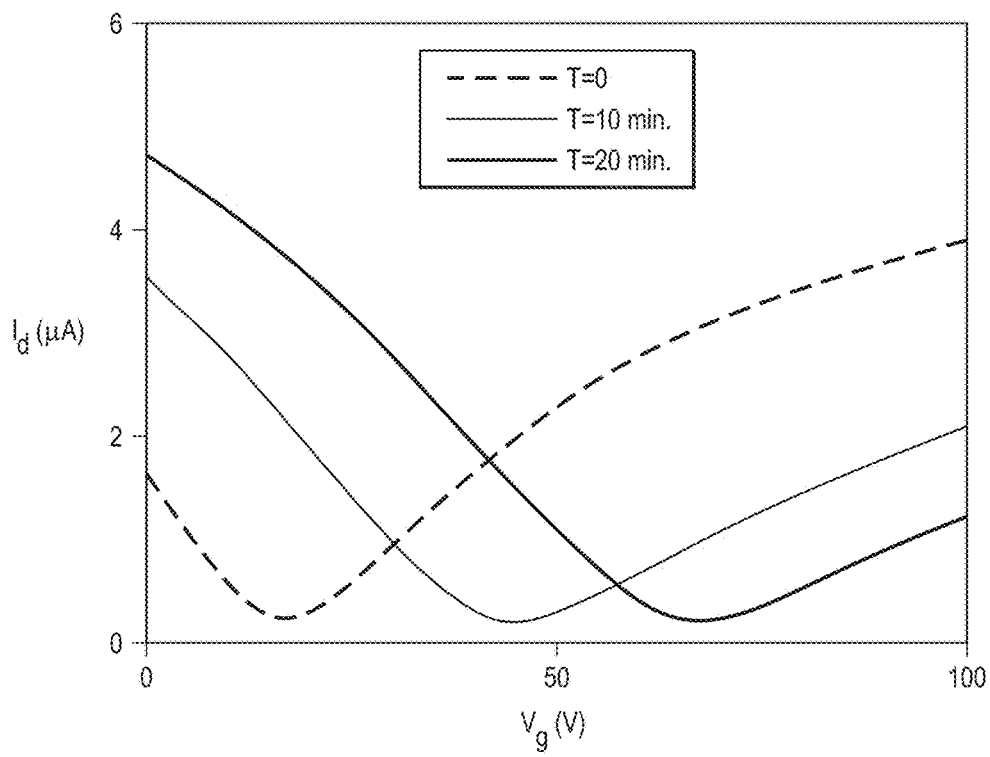
FIGS. 3A-3D illustrate selected elements of data plots showing electronic properties of graphene gas sensors.
Figure 3B:
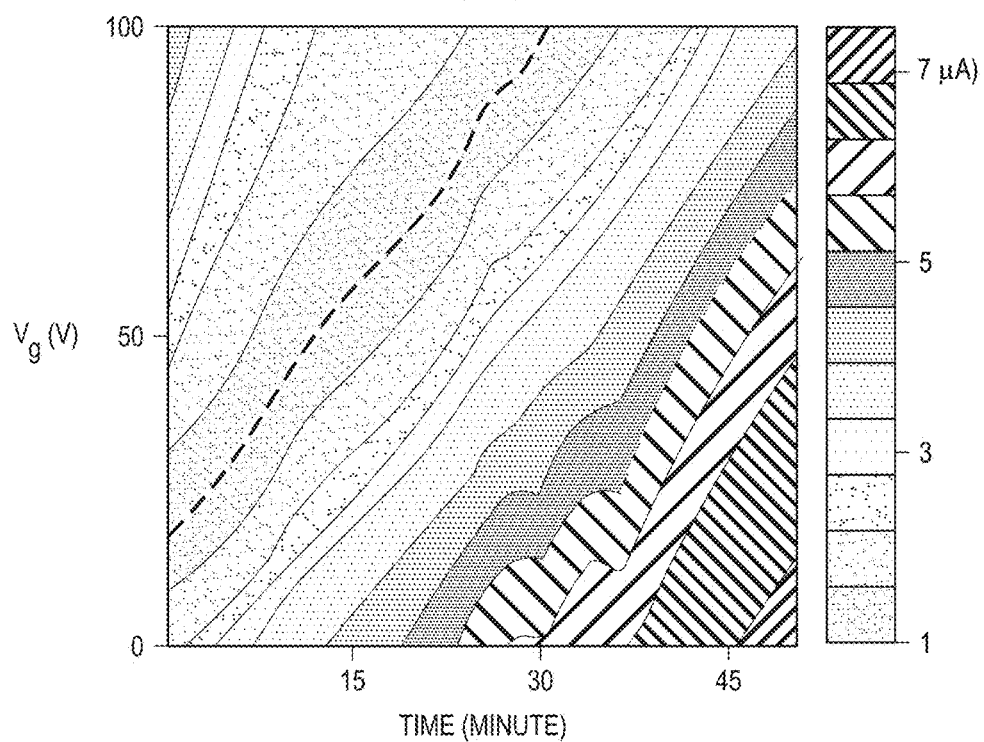
Figure 3C:
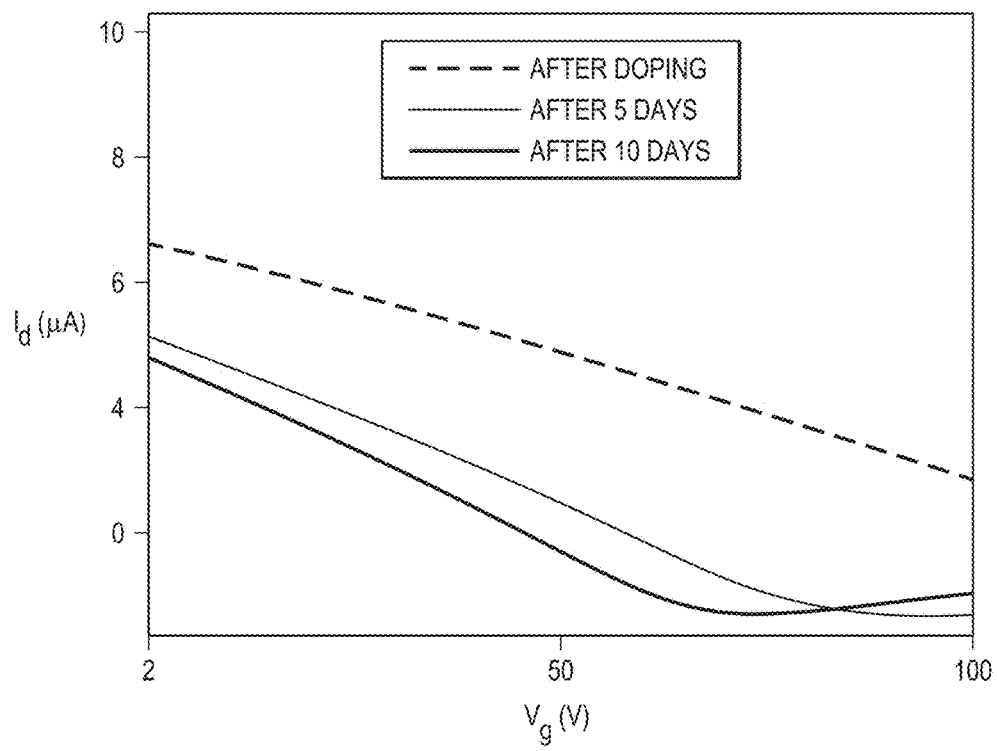
Figure 3D:
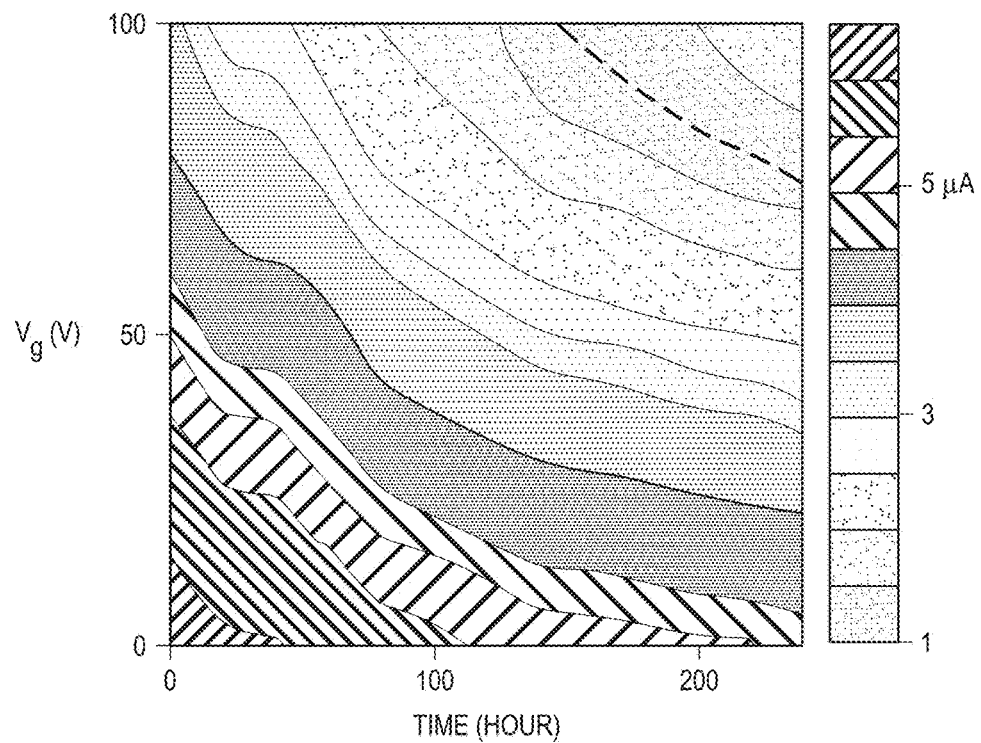

Referring now to FIGS. 3A-3D, selected elements of data plots showing electronic properties of graphene gas sensors are illustrated. Specifically, FIG. 3A shows drain current ($I_d$) as a function of back-gate voltage ($V_g$) for a $NO_2$-doped GFET for different doping durations. FIG. 3B shows a contour plot of $I_d$ as a function of Vg and doping duration. FIG. 3C shows an $I_d$-$V_g$ curve of the GFET during recovery. FIG. 3D shows a contour plot of $I_d$ as a function of $V_g$ and recovery duration over 10 days. In FIGS. 3B and 3D, the source-drain electrical bias is 10 mV and $V_{Dirac}$ is indicated by the dashed line.

To investigate the mechanism of sensitivity enhancement, GFET devices were fabricated and the effect of $NO_2$ adsorbates on electronic properties of graphene was examined. With an applied source-drain electrical bias of 10 mV, the drain current ($I_d$) was measured as a function of back-gate voltage ($V_g$). FIG. 3A shows the $I_d$-$V_g$ curve of the GFET before doping (t=0), and after doping for 10 min. (t=10 min.) and 20 min. (t=20 min.). In various embodiments, the doping may be performed for durations as short as 1 min. and as long as 60 min., or longer in some implementations. Similarly, FIG. 3B shows how the $I_d$-$V_g$ curve evolved over time by exposure to 100 ppm of $NO_2$ in $N_2$ at 500 Torr pressure and room temperature. The dashed line in the contour plots of FIGS. 3B and 3D indicates how $V_{Dirac}$ changed over time. Before $NO_2$ exposure, the graphene channel was hole-doped with $V_{Dirac}$ at 18 V. Under ambient conditions, undoped graphene samples become hole-doped due to adsorption of oxygen and water molecules. Exposure to $NO_2$ gas shifted the Dirac point to higher voltages, which corresponds to enriched concentration of holes.

As $NO_2$ exposure continued, $V_{Dirac}$ became greater than 100 V, beyond the measurement limit. A simple extrapolation suggests that $V_{Dirac}$ was 165V at the end of the doping process with total duration of 50 min. To determine the stability of $NO_2$-doped graphene, another GFET was exposed to 100 ppm of $NO_2$ for 50 min at 500 Torr, and the $I_d$-$V_g$ curve of the $NO_2$-doped GFET was characterized immediately after the doping process. Thereafter, the GFET was kept in the same chamber under vacuum at room temperature for 10 days and the $I_d$-$V_g$ curve was recorded once a day. The results collected in FIGS. 3C and 3D show that $V_{Dirac}$ decreased from 152V to 74V in 10 days, indicating that $NO_2$-doped graphene is somewhat unstable. However, the slow recovery rate corresponds to about 0.1V downshift of the Dirac point voltage over 20 min. This indicates that the change in the Dirac point voltage due to recovery can be neglected in the sensitivity measurements in FIG. 2A.

Figure 4A:
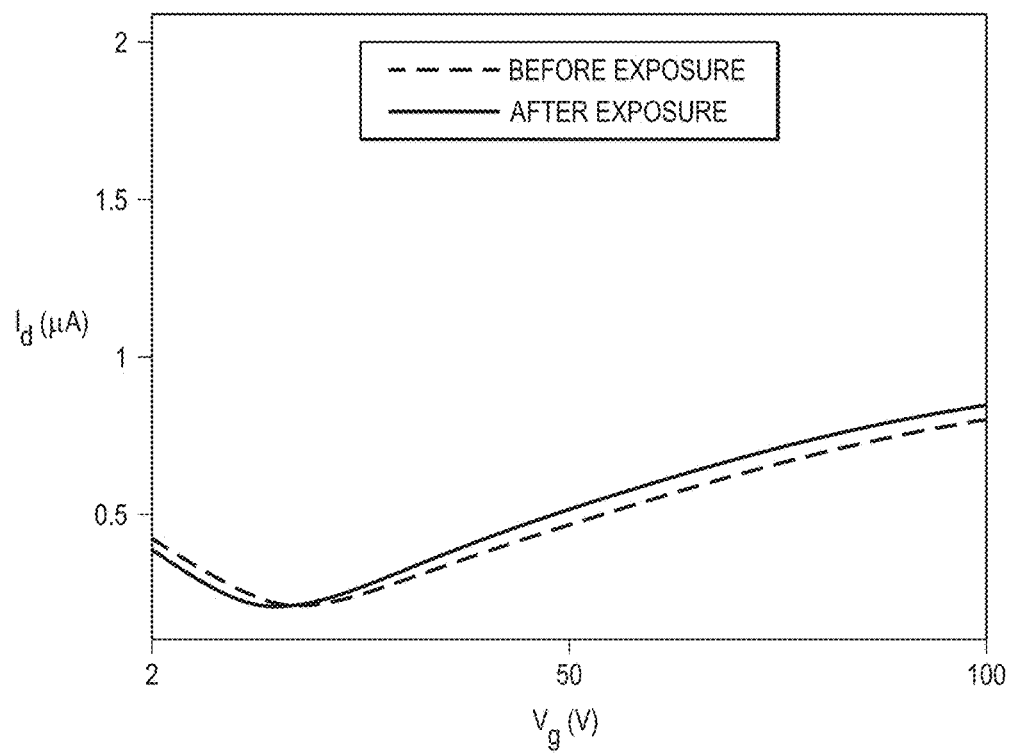
FIGS. 4A and 4B illustrate selected elements of data plots showing electronic properties of graphene gas sensors.
Figure 4B:
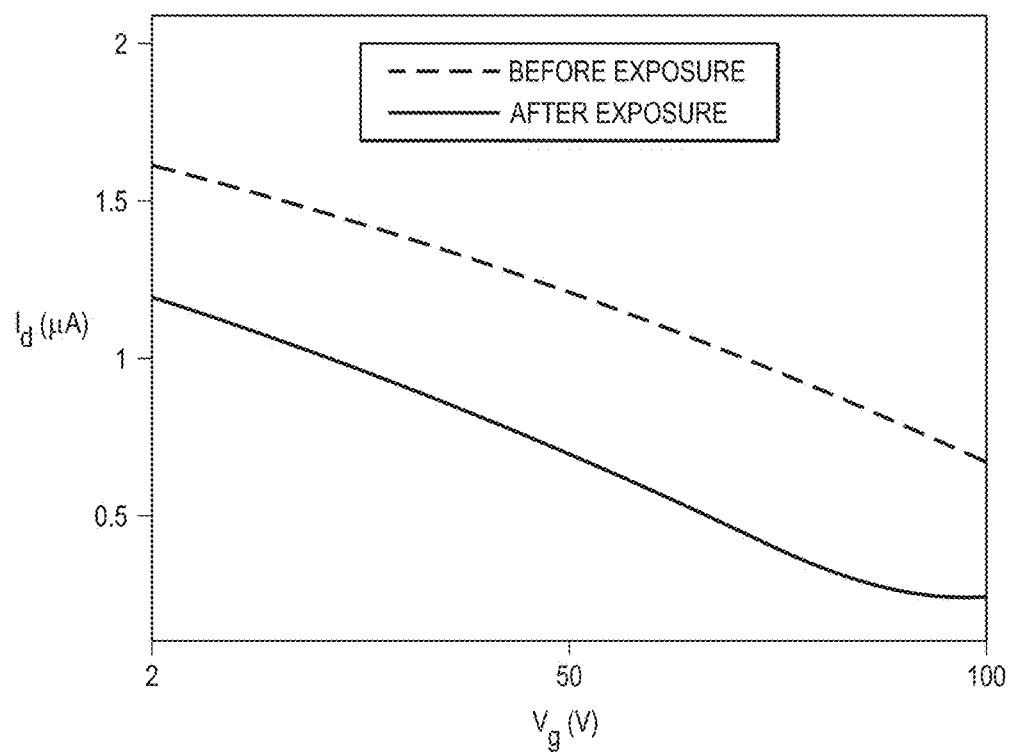

Referring now to FIGS. 4A and 4B, selected elements of data plots showing electronic properties of graphene gas sensors are illustrated. Specifically, FIG. 4A shows an $I_d$-$V_g$ curve of an undoped GFET, and FIG. 4B shows an $I_d$-$V_g$ curve of a $NO_2$-doped GFET before and after exposure to $NH_3$. It was observed that adsorption of $NO_2$ molecules significantly alters the response of the GFET to $NH_3$ exposure. FIG. 4A shows the $I_d$-$V_g$ curve of undoped graphene before and after exposure to 100 ppm of $NH_3$ for 50 min. In FIG. 4A, before exposure to $NH_3$, $V_{Dirac}$ was 18 V, with a slight shift to 15.25V after exposure. FIG. 4B, on the other hand, shows the $I_d$-$V_g$ curve of $NO_2$-doped graphene before and after 50 min exposure to 100 ppm $NH_3$. In FIG. 4B, $V_{Dirac}$ of the GFET was above 100V mainly because $NO_2$-doping shifted $V_{Dirac}$ to high voltages. Simple extrapolation shows that $V_{Dirac}$ of $NO_2$-doped graphene was 144V before and 98V after exposure to 100 ppm of $NH_3$. It is noted that the downshift of Dirac voltage after $NH_3$ exposure cannot be attributed to desorption of $NO_2$ molecules with a recovery rate of about 0.1V over 20 min.

Referring now to FIG. 5, selected elements of Raman spectra of graphene gas sensors are illustrated. Raman spectroscopy can be used to probe structural properties and doping of graphene. Specifically, disorder in $sp^2$ carbon systems can be monitored from the I(D)/I(G) peak intensity ratio from the Raman spectra. Based on theoretical calculations and experimental observations in both top and bottom gated graphene devices, the G peak stiffens indicating that the FWHM(G) decreases for both electron and hole doping. In comparison, the 2D peak stiffens for hole doping and softens (FWHM is increased) for high concentrations of electron doping. In addition, the I(2D)/I(G) peak intensity ratio decreases for both electron and hole doping. Raman spectra of the graphene gas sensors described herein show that graphene became more hole-doped due to exposure to $NO_2$ and no disorder was induced by this process. The peak intensity ratio I(D)/I(G) did not change after transfer to the $SiO_2$/Si substrate and remained similar to the peak intensity ratio I(D)/I(G) of graphene. After doping with $NO_2$, the G peak upshifted by 3.4 $cm^{-1}$ and FWHM(G) decreased by 3.3 $cm^{-1}$. Also after doping with $NO_2$, the 2D peak FWHM was reduced by 2.6 $cm^{-1}$, and the peak intensity ratio I(2D)/I(G) decreased by 42%, as shown in FIG. 5.

Theoretical calculations have shown that $NO_2$ and $NH_3$ molecules are physisorbed onto pristine suspended graphene. According to these studies, charge transfer between the adsorbate and graphene is due to the relative position of the density of states (DOS) of the highest occupied molecular orbital (HOMO) and the lowest unoccupied molecular orbital (LUMO) of adsorbate with respect to the Fermi level of graphene. Another mechanism is hybridization of HOMO and LUMO of adsorbate with graphene orbitals. Theoretical calculations have shown that doping graphene with substitutional dopant atoms induces localized perturbations in the structure and the electronic states near dopant atoms, which provides energetically favorable adsorption sites for gas molecules. Since $NO_2$ molecules are physisorbed onto graphene, no structural disorder is expected to occur for the weak physisorption interaction. On the other hand, several theoretical studies have shown that $NO_2$ adsorption alters electronic states of graphene near the Dirac point. It is believed that the perturbation in the electronic states of graphene that makes graphene more hole-doped and electron-deficient increases the binding affinity and amount of charge transfer for the adsorption of electron-donating $NH_3$ molecules. Similar behavior is expected to occur for adsorption of other electron-donating, closed-shell molecules like carbon monoxide (CO) that weakly physisorb to graphene with long molecule-graphene equilibrium distances comparable to that of $NH_3$-graphene. Therefore, the electronic structure of the adsorbate and adsorbent atoms is scarcely perturbed by the adsorption process and the interaction of the molecule with graphene is a small charge transfer upon adsorption. It is noted that the theoretical calculations on graphene sensors are most relevant for the ideal case of a pristine suspended graphene sample. In the graphene gas sensors described herein, the direct interaction of gas molecules with graphene is suppressed by any residues of organic and water molecules. Therefore, it is contemplated that the sensitivity of graphene to other electron-donating analyte molecules may be enhanced using $NO_2$-doping.

The above discussions suggest that the mechanism of sensitivity enhancement for $NO_2$-doped graphene is comparable to that based on the electric-field effect, where the effect of adsorption of gas molecules on the charge carrier density of graphene can be modified by modulating the Fermi level using the back-gate voltage. The effectiveness of electric field doping for enhancing sensitivity can be compared to that of molecular doping by evaluating the ratio of change of conductance sensitivity $\Delta S = \Delta(\Delta G/G_0)$ to the change of charge carrier concentration $\Delta n$, which is given in Equation 1 below.

$$\frac{\Delta S}{\Delta n} = \frac{qt}{\varepsilon \varepsilon_0} \Delta S / \Delta (V_g - V_{Dirac}) \qquad \text{Equation (1)}$$

In Equation 1:
q is the electron charge;
t is the $SiO_2$ thickness;
$\varepsilon$ is the dielectric constant of $SiO_2$; and
$\varepsilon_0$ is the dielectric constant of vacuum permittivity.

Based on reported values, a graphene $\Delta S/\Delta n$ is about 101 $nm^2$ for 2 min. exposure to 550 ppm of $NH_3$. As measured, $V_g$ is fixed and $\Delta(V_g - V_{Dirac}) = -\Delta V_{Dirac}$. Assuming that sensitivity linearly depends on gas concentration and exposure time (see FIG. 2a), $\Delta S/\Delta n$ for the $NO_2$-doped graphene gas sensor in a similar measurement condition is estimated to be 347 $nm^2$. This suggests that the local effects of adsorbed $NO_2$ molecules on graphene electronic structure may be more effective than the modulation of the Fermi level via the electric-field effect. It is noted that different $\Delta S/\Delta n$ values may be partly due to the difference in thickness of graphene samples, which were monolayer in the $NO_2$-doped graphene gas sensor and few-layer in the back-gated graphene gas sensors, respectively. On the other hand, since the $\Delta S/\Delta n$ values are rather comparable, the mechanism of enhancing sensitivity using $NO_2$-doping of graphene may be comparable to that of electric-field doping of graphene. This also suggests that similar enhancement is expected to occur for the sensitivity of $NO_2$-doped graphene to other electron-donating molecules such as CO, among others. It is noted that for back-gated graphene, sensors obtaining sensitivity values comparable to molecular-doped graphene sensors utilized prohibitively large back-gate voltages that may not be compatible with by many electronic devices and circuits. Many common electronic devices are based on CMOS technology, where the maximum voltage is relatively small, around a few volts.

Using molecular doping, sensitive gas sensors based on graphene and other two-dimensional materials can be developed that can be integrated into CMOS-based electronic devices, which is an important step towards realization of commercial graphene gas sensors.

In summary, the sensitivity of a graphene gas sensor to a gas molecule may be significantly enhanced using molecular doping, which may be as effective as substitutional doping and more effective than electric-field doping. In particular, the room temperature sensitivity of $NO_2$-doped graphene to $NH_3$ was measured to be comparable to the sensitivity of graphene doped with substitutional boron atoms and superior to that of undoped graphene by an order of magnitude. The detection limit for $NO_2$-doped graphene gas sensors was estimated to be about 200 ppb, which may be improved with extended exposure to $NO_2$, compared to a detection limit of about 1.4 ppm for undoped graphene. While the stability analysis of $NO_2$-doped graphene sensors indicates that the doping method may not be completely stable, molecular doping is nevertheless a candidate technique for sensitivity improvement by enhancing the initial carrier concentration. The high levels of doping described herein using molecular doping may be difficult to obtain via the electric field effect in real applications due to restrictions on power consumption and maximum supply voltage, especially for the case of CMOS compatible integrated devices. Electrical characterization and Raman spectroscopy results indicated that the observed sensitivity enhancement was due to localized hole doping of graphene via adsorption of $NO_2$ molecules.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A graphene gas sensor, comprising:
   a graphene element molecularly doped with nitrogen dioxide ($NO_2$);
   a pair of voltage electrodes spaced apart on the graphene element; and
   a pair of current electrodes at each end of the graphene element,
   wherein the graphene element is configured to detect ammonia ($NH_3$) based on a conductivity of the graphene element measured using the pair of voltage electrodes and the pair of current electrodes, and wherein a change in the conductivity upon exposure to $NH_3$ is greater for the graphene element doped with $NO_2$ than an undoped graphene element.

2. The graphene gas sensor of claim 1, wherein the graphene gas sensor is included in a complementary metal oxide semiconductor (CMOS) device.

3. The graphene gas sensor of claim 1, wherein the graphene element is molecularly doped with $NO_2$ using 100 ppm of $NO_2$ in $N_2$ at 500 Torr pressure and at room temperature.

4. The graphene gas sensor of claim 3, wherein the graphene element is molecularly doped for a duration between 10 minutes and 60 minutes.

5. The graphene gas sensor of claim 1, wherein the conductivity is measured by:
   applying a current using the pair of current electrodes;
   measuring a voltage using the pair of voltage electrodes; and
   determining the conductivity based on the current and the voltage.

6. The graphene gas sensor of claim 5, wherein the voltage is measured using a field effect transistor.

7. The graphene gas sensor of claim 1, wherein the graphene element comprises a single atomic layer of carbon.

8. The graphene gas sensor of claim 1, further comprising: a silicon substrate on which the graphene element is situated.

9. A method of detecting ammonia ($NH_3$) gas, the method comprising:
   applying a current to a graphene element molecularly doped with nitrogen dioxide ($NO_2$) using a pair of current electrodes;
   measuring a voltage across the graphene element using a pair of voltage electrodes; and
   exposing the graphene element to $NH_3$ gas while measuring a change in the voltage, wherein the change in the voltage is indicative of the concentration of the $NH_3$ gas, and wherein the change in voltage is greater for the graphene element doped with $NO_2$ than an undoped graphene element.

10. The method of claim 9, wherein the graphene element is implemented in a complementary metal oxide semiconductor (CMOS) device.

11. The method of claim 9, further comprising: molecularly doping the graphene element with $NO_2$ using 100 ppm of $NO_2$ in $N_2$ at 500 Torr pressure and at room temperature.

12. The method of claim 11, wherein molecularly doping the graphene element further comprises: molecularly doping the graphene element for a duration between 10 minutes and 60 minutes.

13. The method of claim 9, further comprising determining a conductivity of the graphene element including:
   applying the current using the pair of current electrodes, spaced apart on the graphene element;
   measuring a voltage using the pair of voltage electrodes, spaced apart on the graphene element; and
   determining the conductivity based on the current and the voltage.

14. The method of claim 13, wherein measuring the voltage further comprises: measuring the voltage using a field effect transistor.

15. The method of claim 9, wherein the graphene element comprises a single atomic layer of carbon.

16. The method of claim 9, wherein the graphene element is situated on a silicon substrate.

* * * * *